United States Patent [19]
Brigham et al.

[11] Patent Number: 6,030,638
[45] Date of Patent: Feb. 29, 2000

[54] PLASMID FOR IN VIVO EXPRESSION OF PROSTAGLANDIN SYNTHASE

[75] Inventors: Kenneth Brigham; Jon T. Conary; Angelo Canonico; Barbara Meyrick, all of Nashville, Tenn.

[73] Assignee: Vanderbilt University, Nashville, Tenn.

[21] Appl. No.: 08/459,493

[22] Filed: Jun. 2, 1995

Related U.S. Application Data

[63] Continuation of application No. 08/080,221, Jun. 21, 1993, abandoned, which is a continuation of application No. 07/746,941, Aug. 19, 1991, abandoned.

[51] Int. Cl.$^7$ .................................................. A61K 9/127
[52] U.S. Cl. ...................... 424/450; 435/455; 435/320.1; 435/325; 435/362; 435/375
[58] Field of Search ................................. 435/320.1, 455, 435/458, 476, 325, 362, 375, 183, 226; 514/44; 424/450, 93.1, 93.21

[56] References Cited

PUBLICATIONS

Bone "The Pathogenesis of Sepsis" Ann. Int. Med. 115(6) 457–469, Sep. 1991.

Orkin et al. Report & Recommendation of the Panel to Assess the NIH Investment in Research on Gene Therapy Dec. 7, 1995.

Hla et al. (1986), Prostaglandins vol. 32 No. 6, pp. 829–845.

DeWitt et al. (1988), Proc. Natl. Acad. Sci. USA 85: 1412–1416.

Andersson et al. (1989), J. Biol. Chem. 264(14): 8222–8229.

Felgner et al. (1987), Proc. Natl. Acad. Sci. USA 84: 7413–7417.

C. M. Gorman et al., *Virology,* 171:371–385 (1989).

A. F. Russo et al., *Neuron,* 1:311–320 (1988).

G. Ciliberto et al., *Cell,* 41:531–540 (1985).

R. M. Abra et al., *Journal of Pharmaceutical Sciences,* 72(2):203–206 (1984).

*Primary Examiner*—David Guzo
*Assistant Examiner*—Jon D Shuman
*Attorney, Agent, or Firm*—Lyon & Lyon LLP

[57] ABSTRACT

A novel plasmid has inserted therein the cDNA for prostaglandin synthase. The present invention further provides a method of increasing prostanoid production in vivo including the general steps of delivering a prostaglandin synthase gene to cells in vivo and hyperexpressing the gene to enhance prostanoid production in the cells.

6 Claims, 4 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 763 base pairs
      (B) TYPE: nucleic acid
      (C) STRANDEDNESS: double
      (D) TOPOLOGY: circular    (ii) MOLECULE TYPE: DNA (genomic)

(iii) HYPOTHETICAL: NO

(iv) ANTI-SENSE: NO

(ix) FEATURE:
      (A) NAME/KEY: promoter
      (B) LOCATION: 1..763

(xi) SEQUENCE DESCRIPTION: SEQ ID NO:1:

```
AATGCATATC GATCTATACA TTGAATCAAT ATTGGCCATT AGCCATATTA TTCATTGGTT      60

ATATAGCATA AATCAATATT GGCTATTGGC CATTGCATAC GTTGTATCCA TATCATAATA     120
```

```
TGTACATTTA TATTGGCTCA TGTCCAACAT TACCGCCATG TTGACATTGA TTATTGACTA      180

GTTATTAATA GTAATCAATT ACGGGGTCAT TAGTTCATAG CCCATATATG GAGTTCCGCG      240

TTACATAACT TACGGTAAAT GGCCCGCCTG GCTGACCGCC CAACGACCCC CGCCCATTGA      300

CGTCAATAAT GACGTATGTT CCCATAGTAA CGCCAATAGG GACTTTCCAT TGACGTCAAT      360

GGGTGGAGTA TTTACGGTAA ACTGCCCACT TGGCAGTACA TCAAGTGTAT CATATGCCAA      420

GTACGCCCCC TATTGACGTC AATGACGGTA AATGGCCCGC CTGGCATTAT GCCCAGTACA      480

TGACCTTATG GGACTTTCCT ACTTGGCAGT ACATCTACGT ATTAGTCATC GCTATTACCA      540

TGGTGATGCG GTTTTGGCAG TACATCAATG GGCGTGGATA GCGGTTTGAC TCACGGGGAT      600

TTCCAAGTCT CCACCCCATT GACGTCAATG GGAGTTTGTT TTGGCACCAA AATCAACGGG      660

ACTTTCCAAA ATGTCGTAAC AACTCCGCCC CATTGACGCA AATGGGCGGT AGGCGTGTAC      720

GGTGGGAGGT CTATATAAGC AGAGCTCGTT TAGTGAACCG TCA                       763

(2) INFORMATION FOR SEQ ID NO:2:

(i) SEQUENCE CHARACTERISTICS:
        (A) LENGTH: 1920 base pairs
        (B) TYPE: nucleic acid
        (C) STRANDEDNESS: double
        (D) TOPOLOGY: circular (ii) MOLECULE TYPE: cDNA to mRNA (ix) FEATURE:
        (A) NAME/KEY: mat_peptide
        (B) LOCATION: 165..1892

(ix) FEATURE:
        (A) NAME/KEY: sig_peptide
        (B) LOCATION: 93..164

(ix) FEATURE:
        (A) NAME/KEY: mRNA
        (B) LOCATION: 1..1920

(xi) SEQUENCE DESCRIPTION: SEQ ID NO:2:

GCGGGCCCGA GGGGCCGGAG CTCCCGGGCA GAGTTAGAGA CGCACTCCAG GAGCCTGAGT       60

CGGTCTCCAG CACGCAACGG CCACCCTGCA CCATGAGCCG GCAGAGTATC TCGCTCCGAT      120

TCCCGCTGCT TCTCCTGCTG CTGTCGCCAT CCCCCGTCTT CTCAGCGGAC CCCGGGGCGC      180

CCGCGCCAGT GAACCCCTGC TGTTACTATC CATGCCAGCA CCAGGGGATC TGTGTTCGCT      240

TCGGCCTTGA CCGCTACCAA TGTGACTGCA CCCGCACGGC TATTCCGGCC CCAACTGCAC      300

CATCCCGGAG ATATGGACCT GGCTCCGGAC GACTTTGCGG CCCAGCCCCT CTTTCATCCA      360

CTTTCATGCT GACGCACGGG CGCTGGCTTT GGGATTTTGT CAATGCCACC TTCATCCGGG      420

ACACGCTCAT GCGTCTGGTA CTCACAGTGC GTTCCAACCT TATCCCCAGC CCTCCCACCT      480

ACAACATAGC GCACGATTAC ATCAGCTGGG AGTCCTTCTC CAATGTGAGC TATTATACTC      540

GCATTCTGCC CTCCGTGCCC CGAGACTGTC CCACGCCCAT GGGCACCAAA GGGAAGAAGC      600

AATTGCCAGA TGCGGAGTTC CTGAGCCGTC GCTTCCTGCT CAGGAGGAAG TTCATCCCTG      660

ACCCTCAAGG CACCAACCTC ATGTTTGCCT TCTTTGCCCA ACACTTCACC CATCAGTTCT      720

TCAAAACTTC CGGCAAGATG GGTCCTGGCT TCACCAAGGC GCTGGGCCAC GGGGTAGACC      780

TCGGCCACAT TTATGGAGAC AATCTGGAAC GTCAGTATCA GCTGCGGCTC TTTAAGGATG      840

GGAAGCTGAA GTACCAGATG CTCAATGGAG AGGTGTACCC GCCATCGGTG GAAGAGGCGC      900

CCGTGCTGAT GCACTACCCC CGGGGCATCC CGCCCCAGAG CCAGATGGCT GTGGGCCAGG      960
```

-continued

```
AGGTGTTTGG GCTGCTTCCT GGGCTCATGC TCTACGCCAC GATCTGGCTG CGTGAGCACA      1020

ACCGCGTGTG TGACCTGCTG AAGGCTGAGC ACCCCACCTG GGGCGACGAG CAGCTCTTCC      1080

AGACGGCCCG CCTCATCCTC ATCGGGGAGA CCATCAAGAT TGTGATAGAG GAGTATGTGC      1140

AGCAGCTGAG CGGCTACTTC CTGCAGCTCA AGTTCGACCC AGAGCTGCTG TTCGGGGCCC      1200

AGTTCCAGTA CCGCAACCGC ATCGCCATGG AGTTCAACCA GCTGTACCAC TGGCACCCGC      1260

TCATGCCCGA CTCCTTCCGG GTGGGCCCCC AGGACTACAG CTACGAGCAG TTTCTGTTCA      1320

ACACCTCCAT GCTGGTGGAC TACGGGTCG AGGCCCTGGT GGACGCCTTT TCTCGCCAGC       1380

CTGCAGGCCG GATTGGTGGG GGTAGGAACA TAGACCACCA CATCCTGCAC GTGGCCGTGG      1440

ATGTCATCAA GGAATCACGG GTGCTGAGGC TGCAGCCCTT CAATGAGTAC CGCAAGAGGT      1500

TTGGCATGAA GCCCTACACC TCTTTCCAGG AGCTCACAGG TGAGAAGGAG ATGGCAGCTG      1560

AATTGGAGGA GCTGTATGGA GACATCGATG CTTTGGAATT CTACCCGGGG CTACTTCTTG      1620

AGAAGTGCCA TCCGAACTCC ATCTTTGGGG AGAGTATGAT AGAAATGGGG GCTCCTTTTT     1680

CCCTTAAGGG CCTCTTAGGA AACCCCATCT GTTCTCCAGA GTACTGGAAG GCGAGCACAT      1740

TTGGCGGTGA GGTGGGCTTC AACCTTGTCA AGACGGCCAC GCTAAAGAAG CTGGTTTGCC      1800

TCAACACCAA GACTTGTCCC TATGTCTCCT TCCACGTGCC AGACCCCCGT CAGGAGGACA      1860

GGCCTGGGGT GGAGCGGCCA CCCACAGAGC TCTGAAGGGG CTGGGCAGCA GCATTCTGGA      1920
```

(2) INFORMATION FOR SEQ ID NO:3:

(i) SEQUENCE CHARACTERISTICS:
        (A) LENGTH: 74 base pairs
        (B) TYPE: nucleic acid
        (C) STRANDEDNESS: double
        (D) TOPOLOGY: circular     (ii) MOLECULE TYPE: DNA (genomic)

(iii) HYPOTHETICAL: NO

(ix) FEATURE:
        (A) NAME/KEY: misc_RNA
        (B) LOCATION: 1..74

(xi) SEQUENCE DESCRIPTION: SEQ ID NO:3:

```
GTTTTTATTT TTAATTTTCT TTCAAATACT TCCATCATGA GTTCTTCACA AAAGAAAGCT       60

GGTGGGAAAG CTGG                                                        74
```

PLASMID FOR IN VIVO EXPRESSION OF PROSTAGLANDIN SYNTHASE

This application is a continuation of application Ser. No. 08/080,221, filed Jun. 21, 1993 abandoned, which is a continuation of application Ser. No. 07/746,941, filed Aug. 19, 1991 abandoned.

This invention was made with Government support under Grant No. HL 45151-01 awarded by the National Institute of Health. The Government has certain rights in the invention.

TECHNICAL FIELD

The present invention provides novel plasmids and methods of using the same for gene therapy and gene therapeutics. More specifically, the present invention provides a means for delivery of the prostaglandin synthase gene in cells proximate to the area in which such a gene might be beneficial.

BACKGROUND OF THE INVENTION

Several approaches have been taken in an attempt to deliver genes to humans for therapeutic purposes. In one approach, lymphocytes have been removed and permanently transformed in vitro using virus vectors. The lymphocytes have been reinfused as transformed cells. Alternatively, adenoviruses have been used to deliver a gene by the airways of an animal, again using retrovirus vectors.

The present invention utilizes a unique plasmid for gene therapy. By way of background, a plasmid is a circular piece of DNA which can function to express genes (pieces of DNA) which have been inserted into the plasmid. Copending applications U.S. Ser. No. 678,027, filed Apr. 1, 1991, now abandoned and U.S. Ser. No. 690,283, filed Apr. 24, 1991, now abandoned disclose plasmids consisting essentially of a small pCMV4 expression vector including a specific coding sequence. Both prior art patents relate to the complexing of these plasmids with liposomes for delivery of the gene to a patient. The liposome includes or is complexed with the expression plasmid incorporated therein, the plasmid being capable of expression extrachromosomally in the cells of a target tissue and being unincorporable into the chromosome of the cells of the target tissue. These plasmids provide a means of treatment for deficiency of a gene product in cells of a target tissue.

Prostaglandin synthase is the proximal enzyme in the conversion of arachidonic acid to several prostanoids. Prostanoids are normally produced ubiquitously in the body and include several highly bioactive substances that are felt to be important in homeostasis. The endothelial prostanoids, prostacyclin and prostaglandin $E_2$ ($PGE_2$) are especially important as these prostanoids have several properties which could be important in preventing or curing disease.

For example, prostacyclin prevents aggregation of platelets, an initial event in clotting in blood vessels. It has been hypothesized that the generation of prostacyclin by the cells lining the blood vessels is necessary and important to prevent clotting under normal circumstances. It is further felt that increased amounts of prostacyclin, particularly in a localized area, can prevent the propagation of clots in small blood vessels as may occur in pulmonary embolus or myocardial infarction. $PGE_2$ is also produced especially by microvascular endothelial cells. $PGE_2$ dilates systemic blood vessels and also inhibits the generation of several cytokines which may be responsible for several of the physiologic and structural consequences of inflammation. If endothelial cells or perhaps other cells in the body can be engineered to produce increased amounts of these protective prostanoids, the result can be therapeutic in a variety of human diseases. Such diseases would include, in addition to pulmonary embolus and myocardial infarction, several diseases of the lungs.

Experimental evidence indicates that prostacyclin and $PGE_2$ may protect the lungs from injury by endotoxin, such as occurs in the clinical syndrome called adult respiratory distress syndrome (ARDS) Brigham et al., Prostaglandin $E_2$ attenuation of sheep lung responses to endotoxin., *J. Appl. Physiol.* 64:2568 (1988). Prostacyclin dilates blood vessels in the lung and has been used in therapeutic trials in the treatment of primary pulmonary hypertension, a disease for which there is no acceptable treatment at the present time. Robin, L., *Clin. Pulmonary Circ. In Health and Disease*; Will, Davison, Weir and Buebrier, eds. Acad. Press, N.Y. pp 491–498 (1987). Prostanoids also dilate airway smooth muscle and therefore could be therapeutic in asthma.

The present invention provides a means for producing hyperexpression of the prostaglandin synthase gene thereby resulting in hyperproduction of prostanoids in cells proximate to an area in which such increases might be beneficial.

SUMMARY OF THE INVENTION

In accordance with the present invention, there is provided a plasmid having inserted therein cDNA for prostaglandin synthase.

The present invention further provides a method of increasing prostanoid production in vivo by delivering a prostacyclin synthase gene to cells in vivo and hyperexpressing the gene to enhance prostanoid production in the cells.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides a plasmid having inserted therein the cDNA for prostaglandin synthase. More specifically, FIG. 1 diagrams the DNA construct. The construct has been designated $PCMV_4$-PGH. The construct is a circular piece of DNA containing a cytomegalovirus derived (CMV) promoter sequence driving the coding region for ovine prostaglandin G/H synthase. In order to increase the expression of the gene, the construct also contains a short translation augmenting sequence and a portion of the 3' untranslated region from the human growth hormone (hGH) gene.

Figure 1:
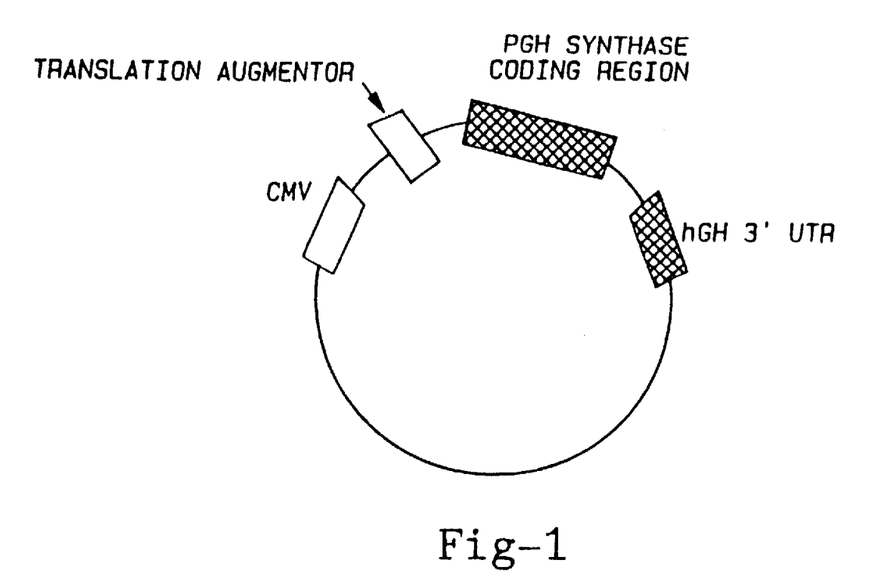
FIG. 1 is a diagram of the plasmid construct made in accordance with the present invention.

As stated above, the plasmid is circular DNA and has a nucleic sequence of 6.8 kilobases nucleic acids. The PGH synthase coding region has a nucleic acid sequence of 1.9 kilobases and has been designated SEQ ID NO: 2. The CMV promoter sequence includes 763 nucleic acids and has been designated SEQ ID NO: 1. The translation augmenter includes 74 bases nucleic acids and has been designated as SEQ ID NO: 3. The hG 3' UTR sequence includes 624 nucleutides.

The plasmid made in accordance with the present invention was prepared by the following method: The present invention utilizes polymerase chain reaction (PCR) amplification and "linker primers" (FIG. 7) to insert the coding sequence of PGH synthase into the pCMV4 expression vector. This method consists of synthesizing two oligonucleotide primers (20–30 nucleotides in length). One oligonucleotide is homologous to the 5' untranslated region immediately upstream (5') of the initiation codon and the second oligonucleotide is complementary to the 3' untranslated region immediately downstream (3') of the stop transcription codon. Both oligonucleotides have a one or two base substitution which creates a unique (and different) restriction enzyme site in the untranslated regions of the amplified gene. The 5' and 3' oligonucleotides were designed such that they created a restriction enzyme site approximately 8 nucleotides downstream from the 5' end of the oligonucleotide. Both of these requirements are critical, the former to insure a restriction enzyme site which is recognizable and cleavable and the latter to insure that the reading frame of the gene is not altered.

After the primers were designed, they were synthesized by the Vanderbilt University Molecular Biology Core Laboratory. The reading frame of the gene of interest was amplified using Vent DNA polymerase, 100 ng of target DNA, a programmable temperature cycler, and standard reaction conditions (denaturing at 93.5°, annealing at 56° and extension at 75°). Vent DNA polymerase was used because it has a 3' to 5' proofreading activity in addition to enhanced stability at high temperature and a highly specific and processive 5' to 3' DNA polymerase activity. After PCR amplification, the unique restriction sites were cleaved with the appropriate restriction enzymes, the amplified gene was separated from the small fragments released by the action of the restriction enzymes and from unincorporated primers and nucleotides by gel filtration through a S-400 spin column. The amplified genes which now had cloning sites on each end were ligated into pCMV4 which had been previously cleaved with the same restriction enzymes which were utilized to prepare the cloning sites on the amplified gene.

Figure 7:
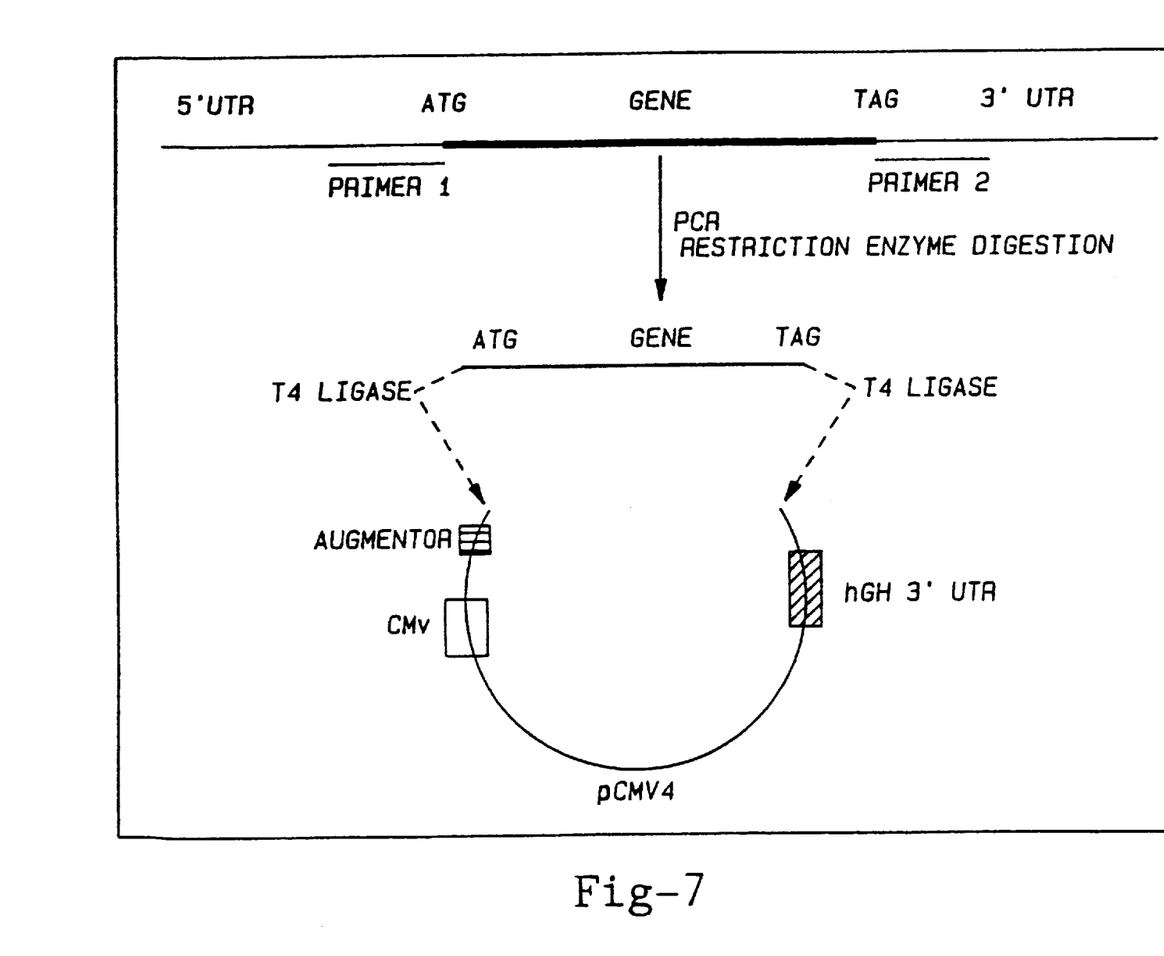
FIG. 7 is a schematic representation of a linker primer made in accordance with the present invention.

The pCMV4 vector was selected for expression constructs because it represents a "state of the art" expression vector. In particular, this vector provides a stable mRNA through the use of human growth termination and poly-adenylation signals. This vector also provides sequences from the alfa Mosiac virus 4 which act as a translational augmenter by decreasing the requirement for initiation factors in protein synthesis. In addition, this construct also contains a polylinker region and the promotor-regulatory region of the human cytomegalovirus major immediate early gene (FIG. 7).

After ligation, the pCMV4-PGH construct was transfected into fresh competent bacteria (*E. coli* NM522). The competent bacteria was prepared by standard methods (Hanahan, D., *J. Molecular Biology*, 166:557–580 (1980)). After transfection the bacteria was plated out on plates containing carbenicillin, an ampicillin analog. This provides selection pressure for bacteria which contained the pCMV4 construct. The plasmid carries the gene for ampicillin resistance. After the bacteria which harbor the plasmid have grown into distinct colonies several of the colonies are grown up as individual 5 ml liquid cultures. An aliquot of the liquid cultures is stored and the rest is processed as a "mini" prep. It was then confirmed that the isolated plasmid contains the inserted piece of DNA by performing both a dot blot analysis and by releasing the inserted piece of DNA by performing a restriction enzyme digest. The restriction enzyme digest should yield both the linearized plasmid and the original piece of DNA.

Once a colony has been isolated which contains the piece of cloned DNA, a large scale plasmid preparation is grown. The plasmid is purified by lysis of the bacteria and precipitation of the plasmid with polyethylene glycol and then purified an additional time by ultracentrifugation in an isopynic CsCl solution. After ultracentrifugation for 40 hours at 45,000 rpm, the purified plasmid is withdrawn through the side of the tube and the ethidium bromide is removed by extraction with TE saturated butanol. Finally, the isolated plasmid is precipitated with ethanol and resuspended in sterile water. This double purification procedure (polyethylene glycol and CsCl) appears to be critical to minimize endotoxin contamination.

The construction of the pCMV4-PGH vector was a culmination of 15 years of work with plasmid DNA. Of significant importance to this development was the development of the polymerase chain reaction (PCR) procedure by Siedase. However, there were two problems with the PCR which had to be overcome. First, the original PCR method utilized Taq DNA polymerase (Siedase), an enzyme purified from Thermatus aquaticus. While this enzyme performed well in the role of DNA amplification, it does not have any proofreading capability (3' to 5' exonuclease). The lack of proofreading ability and reasonably high rate of base mis-incorporation makes it difficult to clone a PCR product and be assured of an authentic copy. The advent of Vent DNA polymerase (New England Bio Labs), a different high temperature DNA polymerase which has proofreading activity, alleviated these problems.

A second problem encountered with cloning PCR products is the lack of an easily clonable piece of DNA after PCR amplification. The amplification process routinely leaves a 3' overhang of either an A or T nucleotide. The overhanging bases can be removed by the action of one of several DNA exonucleases. The problem is, however, that this approach yields a piece of DNA with two "blunt" ends. Blunt end cloning is more difficult to accomplish and prevents directional cloning. The present invention overcame this problem by utilizing "linker-primers" as discussed herein. Applicant designed specific restriction enzyme sites into applicant's PCR primer such that applicant could achieve directional cloning of the amplified DNA.

The development of Lipofectin (Bethesda Research Laboratories) provided applicant with the means to transfect cells or animals with a plasmid without the manipulation and potential harm inherent to such procedures as electroporation or calcium phosphate precipitation. Applicant demonstrates first with cells and then with mice that plasmid construct containing a reporter gene could be transfected via Lipofectin and that the transfected gene could be expressed. Additional studies confirmed that non-reporter genes (prostaglandin G/H synthase, PGH) could be expressed in endothelial cells after Lipofection. The next step was to transfect animals with the pCMV4-PGH construct to determine if this method could be utilize to deliver a gene of physiological importance.

Applicant has demonstrated expression of the prostaglandin synthase gene using a construct delivered intravenously to rabbits. The intravenous injection of the cDNA construct complexed to liposomes resulted in increased generation of endothelial derived prostanoids $PGE_2$ and prostacyclin as shown in FIG. 2.

The preferred liposome used in accordance with the present invention is lipofectin (Bethesda Research Laboratory) which provided applicant with the means to transfect cells or animals with the plasmid without the manipulation and potential harm inherent to such procedures as electroporation or calcium phosphate precipitation.

The plasmids were complexed to the liposomes by the following procedure. For in vivo studies in rabbits the DNA is administered at a dose of 500 µg/kg as a complex with Lipofectin. The DNA (500 µg) is brought up to a volume of 2.5 ml of sterile water and combined with 2.5 ml of Lipofectin (a ratio of 1:5 DNA to Lipofectin). The DNA/Lipofectin mixture is gently mixed and allowed to equilibrate for 10 to 15 minutes. Extreme care is exercised to prevent any negative pressure on the mixture as this tends to result in the precipitation of the DNA:Lipofectin complex. The DNA:Lipofectin complex is then slowly administered to the animal by intravenous injection. The success of the transfection is determined by analyzing the animal's tissue for the presence of the mRNA synthesized from the plasmid and by immunohistochemical staining.

Figure 2:
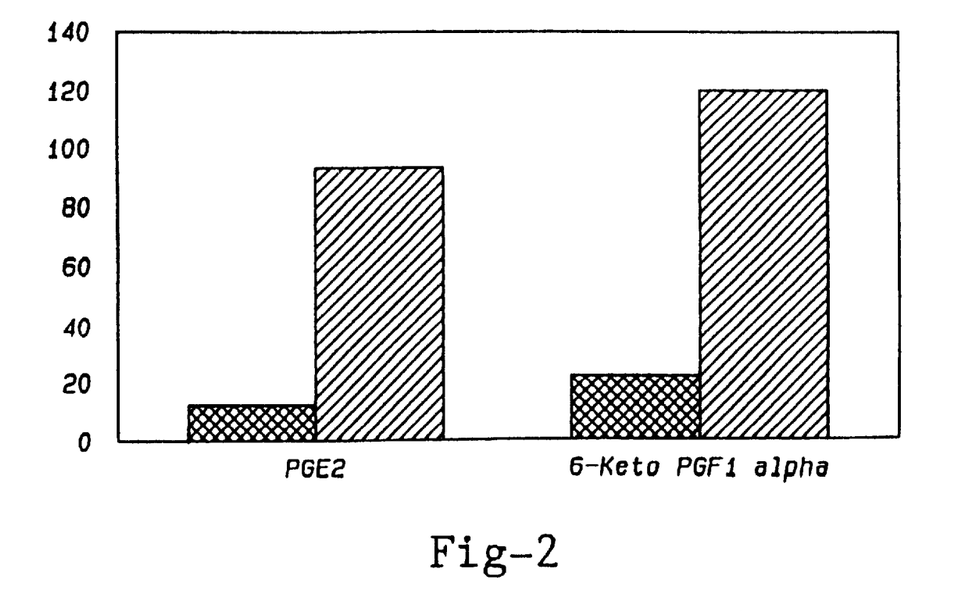
FIG. 2 is a graph showing production of prostacyclin by the lungs of rabbits.

Referring specifically to FIG. 2, the graph shows prostacyclin production by the lungs of rabbits removed two days following intravenous injection of either the $PCMV_4$-PGH or $PCMV_4$ (control) complex to liposomes. That is, rabbits were intravenously injected with the plasmid including the cDNA construct for the prostaglandin synthase or a control including only the plasmid. In each case, 500 µg of DNA and 2500 µg of liposomes complexed as detailed above was injected. After two days, lungs were removed, minced, incubated overnight (24 hours) in medium 199, and 6-Keto $PGF_{1\alpha}$, the stable metabolite of prostacyclin, and $PGE_2$ levels were measured in medium by ELISA. Lungs from animals receiving the $PCMV_4$-PGH plasmid produced greater amounts of prostanoids than did control lungs.

This experiment showed the general concept that pursuant to the present invention and method, a prostaglandin synthase gene can be delivered to cells in vivo and the gene can hyperexpress to enhance prostanoid production in the cells. This was specifically shown as an increased generation of the endothelial derived prostanoids $PGE_2$ and prostacyclin as shown in FIG. 2.

Figure 3:
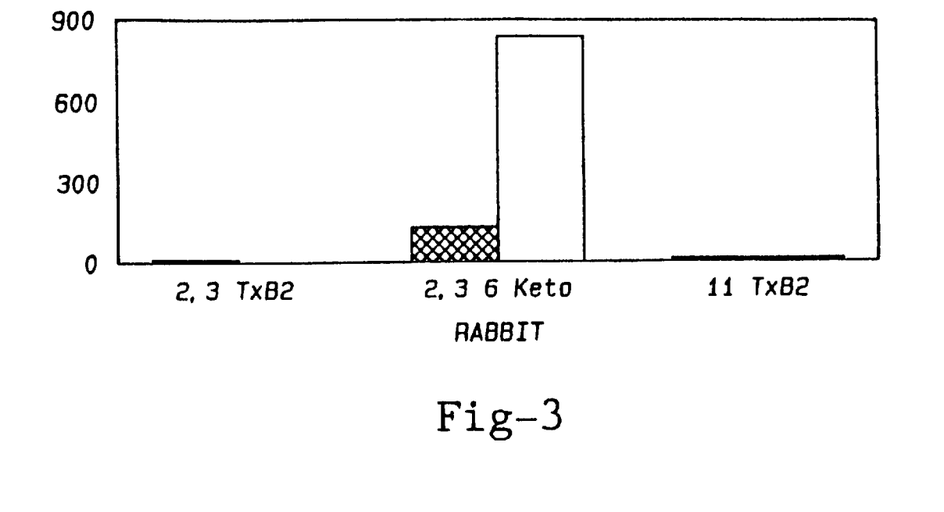
FIG. 3 shows measurements of urinary thromboxane and prostacyclin metabolites in rabbits.

As shown in FIG. 3, urine collected from rabbits two days following injection of the DNA liposome complex made in accordance with the above described method demonstrates increased amounts of prostacyclin metabolite without increased amounts of thromboxane $B_2$, a prostanoid derived principally from other then endothelial cells. More specifically, measurements were made of urinary thromboxane and prostacyclin metabolites in a rabbit two days after in vivo lipofection with either $PCMV_4$-PGH or the unmodified $PCMV_4$ vector. The animal receiving $PCMV_4$-PGHS had large amounts of prostacyclin metabolite (2,3,6-Keto) in its urine. Meanwhile, thromboxane metabolites were not elevated. This demonstrates the specificity of the present invention to cause an increased generation of endothelial derived prostanoids as opposed to prostanoids such as thromboxane $B_2$, a prostanoid derived principally from all other than endothelial cells.

Experiments were performed to determine whether animals expressing the prostaglandin synthase gene responded to a stimulus different from normal. This was tested by injecting such animals with endotoxin. Two days after transfection with either pCMV4 or with pCMV4-PGH the animals (New Zealand white rabbits) were placed in a plastic rabbit restraint. A baseline blood sample (1 to 2 ml) was drawn from a small artery in the ear of each rabbit and this sample was used to obtain a white blood cell count, a blood gas, and was analyzed by ELISA for PGE2 and prostacyclin concentration. In order to insure that the blood samples provided an accurate measure of the prostanoids the samples were immediately treated with indomethacin to prevent any further PGH synthase activity.

After the baseline samples were obtained, the animals were given a dose (1 µg/kg) of endotoxin. This dose was administered over 4 minutes. Blood samples were taken and handled as described above every 15 minutes for 90 minutes. One hour and forty-five minutes after the endotoxin was given to the rabbits, the rabbits were given sodium pentobarbital (1000 U/ml) 1 part pentobarbital to 2 parts heparinized saline and a total dose of 4–6 ml was given to each animal. Liver, lung and kidney were then surgically removed from each animal and analyzed for mRNA and DNA as described above.

In addition, one gram of each organ was carefully cut into 1 to 2 mm slices and placed in 2 ml of medium (M199) supplemented with antibiotics. These organ slices were incubated at 37° C. for 24 hours in 5% $CO_2$ and then the medium was removed and the prostanoid content was determined by ELISA.

Figure 4:
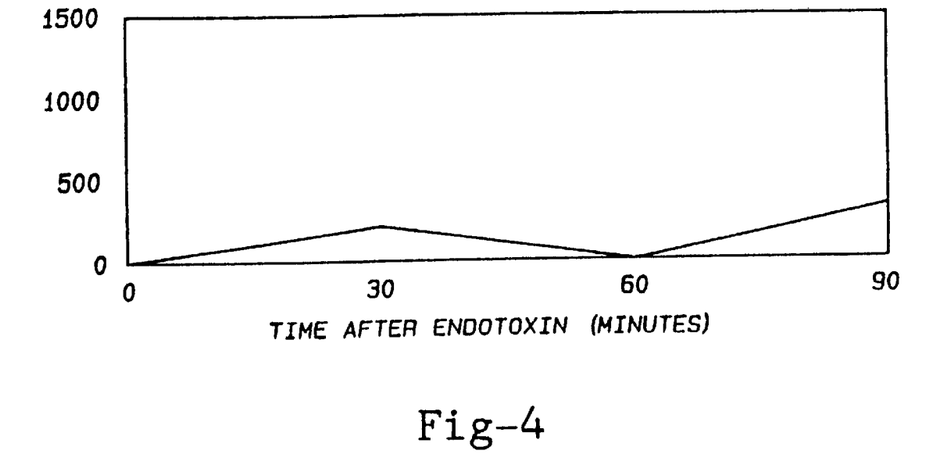
FIG. 4 is a graph showing plasma $PGF_{1\alpha}$ versus time after endotoxin infusion.
Figure 5:
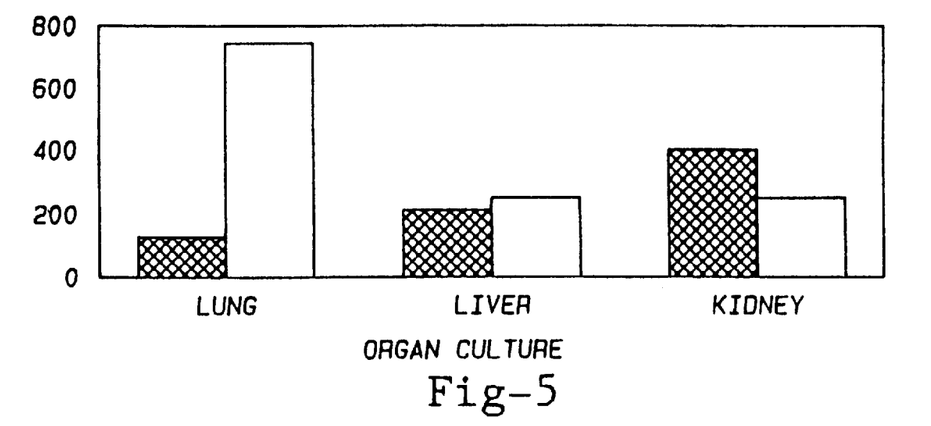
FIG. 5 is a graph showing in vivo lipofection of PGH synthase in rabbits.

FIGS. 4 and 5 illustrate data from the aforementioned experiments. In FIG. 4, the effects are shown of endotoxin infusion on plasma concentrations of prostacyclin metabolite (6-keto $PGF_{1\alpha}$) in rabbits two days after in vivo lipofection with either $PCMV_4$-PGH or the unmodified $PCMV_4$ vector. The data shows that the animal receiving $PCMV_4$-PGH had higher baseline prostacyclin plasma concentrations and the response to endotoxin was exaggerated.

More specifically, in FIG. 4, blood concentrations of the prostacyclin metabolite 6-Keto $PGF_{1\alpha}$ are shown in animals two days following injection of either the prostaglandin synthase DNA construct made in accordance with the present invention or a control plasmid devoid of the prostaglandin synthase gene. Two days following injection, animals were injected with endotoxin and concentrations of the prostacyclin metabolite were measured in blood over 90 minutes. As shown in the illustration of FIG. 4, the baseline concentration of the prostacyclin metabolite in plasma was higher in the animal receiving the prostaglandin synthase DNA construct and responses of plasma prostacyclin levels to endotoxin were greatly exaggerated.

The data in FIG. 5 shows prostanoid generation by organs removed from the animals 90 minutes following endotoxin infusion, as detailed in FIG. 4, and incubated for 24 hours in organ culture. Organ minces were incubated for 24 hours and prostacyclin metabolite (6-Keto $PGF_{1\alpha}$) concentrations measured in the medium by ELISA. Increased prostacyclin production appeared to be specific for the lung of the animal which received the $PCMV_4$-PGH construct. The data in FIG. 5 specifically shows that the lungs from animals which had received the PGH synthase gene produced dramatically higher amounts of prostacyclin than did the lungs from control animals. The prostacyclin production appears to be specific for the lungs, since organ cultures from liver or kidney did not produce increased amounts of prostanoids.

In order to determine whether organs other than the lung could be made to hyperexpress the prostaglandin synthase gene, the prostaglandin synthase DNA construct completed to liposomes was injected directly into the left renal artery of the rats. The animals were killed two days later. Organs were removed, minced, cultured overnight, and the concentrations of prostacyclin metabolite were measured.

Figure 6:
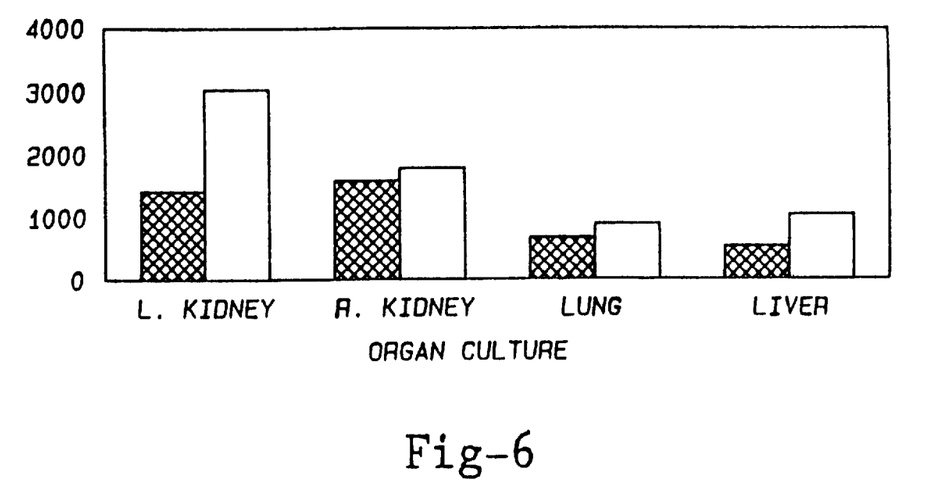
FIG. 6 shows the amounts of 6-Keto $PGF_{1\alpha}$ two days post transfection.

Referring to FIG. 6, the injected kidney from the animal receiving the prostaglandin synthase DNA produced increased amounts of prostacyclin whereas the noninjected kidney from the same animal did not. The lung, liver and left kidney from the control animal showed prostaglandin generation similar to uninjected organs in the animal receiving the PGH synthase gene. This suggests that tissue specific expression of the $PCMV_4$-PGH vector can be obtained by choosing the injection site.

In view of the above, applicant has demonstrated tissue specific routes of delivery for a DNA construct of a plasmid having inserted therein a cDNA for prostaglandin synthase resulting in hyperexpression of the gene in the selected tissue. This method of delivery for enhancing prostanoid production in cells proximate to an area in which such increases in production might be beneficial is quite valuable for gene therapy.

The present invention further provides a novel design of PCR primers and the use of Vent DNA polymerase. In general, the PCR primers are designed with restriction enzyme sites on their 5' end. In accordance with the present invention, there is provided restriction enzyme sites 8 bases downstream from the 5' end of the primer. Applicant has created the restriction enzyme site by a single or at most 2 base change. This insures that if the restriction enzyme requires some 5' nucleotides to insure its three dimensional structure that a sufficient number of bases are provided for that purpose. Secondly this approach eliminates any problems which may develop from the presence of over-hang after the PCR reaction. This approach further provides the use of Vent DNA polymerase. This enzyme which has both a 3' to 5' proofreading capability and more stability at high temperature increases the number of amplified DNA which are accurate copies of the original template.

A further novel aspect of the present invention is the pCMV4-PGH construct, per se. First, these plasmids remain extrachromosomal in eucaryotic organisms. Accordingly, many of the problems associated with the use of retroviruses are solved, such as incorporation into the host genome, risk of mutation of an important gene, etc. Secondly, because the plasmid remains extrachromosomal and does not replicate in eucaryotes, this method of gene delivery is transient. Third, applicant has demonstrated herein successful transfection of both cells and animals with this construct. A recent search of the literature revealed approximately 20 published examples of direct delivery of a gene in vivo (Felgner, P.L. et al., Nature 349:351–352, 1991). The vast majority of these examples were reporter genes and the only genes demonstrating expression after liposome mediated delivery were reporter genes. Herein is demonstrated not only the direct delivery of a gene in vivo but the enhanced production of the protein product.

The invention has been described in an illustrative manner, and it is to be understood that the terminology which has been used is intended to be in the nature of words of description rather than of limitation. obviously many modifications and variations of the present invention are possible in light of the above teachings. It is, therefore, to be understood that within the scope of the appended claims, the invention may be practiced otherwise than as specifically described.

What is claimed is:

1. A method of increasing prostanoid production in vivo comprising the steps of delivering a prostaglandin synthase gene to cells in vivo; and hyperexpressing the gene to enhance prostanoid production in the cells.

2. The method as set forth in claim 1 further comprising the steps of first inserting a cDNA for prostaglandin synthase into a plasmid, complexing the plasmid with a liposome carrier and delivering the liposome carrier to the cells.

3. The method as set forth in claim 1 where said step of delivering a prostaglandin synthase gene to cells in vivo comprises intravenously injecting the gene as a cDNA construct complexed to liposome.

4. The method as set forth in claim 1 comprising the step of increasing the generation of endothelial derived prostanoids, PGE2 and prostacyclin.

5. The method as set forth in claim 1 wherein said step of delivering prostaglandin synthase gene to cells in vivo comprises injecting the gene as a cDNA construct complexed to liposome into an artery supplying an organ and hyperexpressing the gene in the organ.

6. The method as set forth in claim 2 wherein the plasmid comprises a pCMV4 expression vector comprising a cDNA for prostaglandin synthase.

* * * * *